United States Patent [19]

Rentzea et al.

[11] Patent Number: 5,389,656
[45] Date of Patent: Feb. 14, 1995

[54] ACETYLENE DERIVATIVES, THEIR PREPARATION AND THEIR USE FOR CONTROLLING INSECTS AND ACARIDAE

[75] Inventors: Costin Rentzea, Heidelberg; Uwe Kardorff, Mannheim; Christoph Kuenast, Otterstadt; Hans Theobald, Limburgerhof; Thomas Kuekenhoehner, Frankenthal, all of Germany

[73] Assignee: BASF Aktiengesellschaft, Ludwigshafen, Germany

[21] Appl. No.: 911,386

[22] Filed: Jul. 13, 1992

Related U.S. Application Data

[63] Continuation of Ser. No. 737,866, Jul. 30, 1991, abandoned.

[30] Foreign Application Priority Data

Jul. 31, 1990 [DE] Germany .................... 4024281

[51] Int. Cl.⁶ ............... C07D 277/22; C07D 333/08; A01N 43/78; A01N 43/10
[52] U.S. Cl. .................... 514/365; 514/438; 548/202; 548/203; 549/74; 549/78; 549/80
[58] Field of Search ............ 548/202, 203; 549/74, 549/78, 80; 514/365, 438

[56] References Cited

U.S. PATENT DOCUMENTS 4,788,207 11/1988 Lutomski et al. .................... 514/365
4,889,867 12/1989 Lutomski et al. .................... 514/365

FOREIGN PATENT DOCUMENTS 81123903  9/1981  Japan .................... 548/196
81154401 11/1981  Japan .................... 548/196
88/00467  1/1988  WIPO .

OTHER PUBLICATIONS

Organometallic Chem. 93 (1975).
Tetrahedron 40 (1984), 2773 et seq.
Agric. Biol. Chem. 46 (1982), 309 et seq.
JA 81/123903 Chem. Abstr. 96 (1982), 16085 z.
Chem. Pharm. Bull., 29(12) 3548–3553 (1981).
J. Het. Chem., 19, 145–151 (1982).
Chemical Abstracts, 93(7), 71446 (1980).
Chemical Abstracts, 106(21), 176241 (1987).
Chem. Pharm. Bull., 29(12), 3543–3547 (1981).
Chemical Abstracts, vol. 72 (5), entry 21696 (1970).
J. Chem. Soc. Part 1, vol. 20, 2241–2249 (1973).
Chem. Pharm. Bull., 35(2), 823–828 (1987).
D'auria, J. org. Chem 55, 4019 (1990).

Primary Examiner—Robert Gerstl
Attorney, Agent, or Firm—Keil & Weinkauf

[57] ABSTRACT

Acetylene derivatives of the Formula I $$R^1-C\equiv C-R^2 \qquad \text{I}$$

where $R^1$ is an unsubstituted or substituted five-membered heteroaromatic structure and $R^2$ is an unsubstituted or substituted mononuclear to trinuclear aromatic ring system, their preparation, insecticides and acaricides containing them and methods for their use.

2 Claims, No Drawings

ACETYLENE DERIVATIVES, THEIR PREPARATION AND THEIR USE FOR CONTROLLING INSECTS AND ACARIDAE

This is a continuation of Ser. No. 07/737,866, Jul. 30, 1991, now abandoned.

The present invention relates to acetylene derivatives of the general formula I $$R^1—C\equiv C—R^2 \qquad \text{I}$$

where $R^1$ is a five-membered heteroaromatic structure which contains from one to three nitrogen atoms and/or an oxygen or sulfur atom as hetero atoms and may carry from one to three of the following radicals: nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_3$–$C_6$-alkenyl or $C_3$–$C_8$-cycloalkyl, $R^2$ is a mononuclear to trinuclear aromatic ring system which may carry from one to five halogen atoms and/or from one to three of the following groups: nitro, cyano, $C_1$–$C_6$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkoxycarbonyl, $C_3$–$C_6$-alkenyl, phenyl or phenoxy, where the last-mentioned aromatic groups may in turn carry from one to five halogen atoms and/or from one to three of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio, and $R^1$ is not 2-thienyl when $R^2$ is phenyl or 4-methylphenyl.

The present invention furthermore relates to a process for the preparation of these compounds and to insecticides and acaricides containing them and to methods for controlling insects and acaridae with the aid of acetylene derivatives of the formula IA $$R^1—C\equiv C—R^2 \qquad \text{IA}$$

where $R^1$ is a five-membered heteroaromatic structure which contains from one to three nitrogen atoms and/or an oxygen or sulfur atom as hetero atoms and may carry from one to three of the following radicals: nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_3$–$C_6$-alkenyl or $C_3$–$_8$-cycloalkyl, $R^2$ is a mononuclear to trinuclear aromatic ring system which may carry from one to five halogen atoms and/or from one to three of the following groups: nitro, cyano, $C_1$–$C_6$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkoxycarbonyl, $C_3$–$C_6$-alkenyl, phenyl or phenoxy, where the last-mentioned aromatic groups may in turn carry from one to five halogen atoms and/or from one to three of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio.

The literature discloses 1-phenyl-2-thienylacetylene derivatives as nematocides [Organometallic Chem. 93 (1975), 259 et seq.; Tetrahedron 40 (1984), 2773 et seq.; Agric. Biol. Chem. 46 (1982), 309 et seq.; JP-A 81/123,903 [Chem. Abstr. 96 (1982), 16085 z]].

It is an object of the present invention to provide novel active insecticides and acaricides.

We have found that this object is achieved by the acetylene derivatives I defined at the outset. We have also found processes for the preparation of these acetylene derivatives, insecticides and acaricides containing them and methods for their use.

The acetylene derivatives I are obtainable by various methods. They are particularly advantageously obtained by one of the processes A and B described below.

Process A

Acetylene derivatives of the formula I are obtained, for example, by reacting an alkyne of the general formula IIa or IIb with an aryl halide of the general formula IIIa or IIIb in a conventional manner in an inert organic solvent in the presence of a base and of a palladium and copper catalyst.

$$R^1—C\equiv C—R + R^2—Hal \longrightarrow R^1—C\equiv C—R^2$$
$$\text{IIa} \qquad \text{IIIb} \qquad \text{I}$$

$$R—C\equiv C—R^2 + R^1—Hal \longrightarrow R^1—C\equiv C—R^2$$
$$\text{IIb} \qquad \text{IIIa} \qquad \text{I}$$

In formulae IIa and IIb, R is hydrogen or a $(C_1$–$C_3$-alkyl$)_2$C(OH) protective group, such as 2-hydroxypropyl, 2-hydroxybutyl or 3-hydroxypentyl.

In formulae IIIa and IIIb, Hal is halogen, such as fluorine, chlorine, bromine or iodine, in particular bromine or iodine.

The reaction of IIa, b with IIIa, b is carried out in general in an inert organic solvent, in the presence or absence of water and in the presence of a palladium catalyst and of a copper catalyst and of a base, and in the presence of absence of a phase transfer catalyst at from −10° to 150° C., in particular from 20° to 150° C.

The reaction usually takes place at a sufficient rate at above 20° C. In general there is no need to exceed 120° C. Since the reaction takes place in many cases with evolution of heat, it may be advantageous to provide a means of cooling.

Examples of suitable solvents are hydrocarbons, such as pentane, hexane, benzene, toluene and xylenes, ethers, such as diethyl ether, di-n-butyl ether, methyl tert-butyl ether, tetrahydrofuran and dioxane, ketones, such as acetone and methyl ethyl ketone, nitriles, such as acetonitrile, alcohols, such as methanol and ethanol aprotic solvents, such as dimethyl formamide, dimethyl sulfoxide and pyridine, in particular acetonitrile, ethanol, dimethylformamide and corresponding mixtures.

Usually not less than equivalent amounts of a base are used, but the latter may also be used in excess or, if required, as a solvent.

Examples of suitable bases are hydroxides of alkali and alkaline earth metals, such as sodium hydroxide, potassium hydroxide and calcium hydroxide, alcoholates of alkali and alkaline earth metals, such as sodium methylate, sodium ethylate, calcium methylate or potassium tert-butylate, alkali or alkaline earth metal hydrides, such as sodium hydride, potassium hydride or calcium hydride, alkali or alkaline earth metal carbonates, such as sodium carbonate, potassium carbonate or calcium carbonate, aliphatic amines, such as dimethylamine, triethylamine, tripropylamine, tributylamine or pyrrolidine, and aromatic amines, such as pyridine, N,N-dimethylaniline and N,N-diethylaniline.

The catalysts used are palladium compounds, such as palladium chloride, palladium acetate, bis-(triphenylphosphine)-palladium acetate, bis-(triphenylphosphine)-palladium chloride, bis-(triphenylphosphine)-palladium bromide, palladium-bis-(acetonitrile) dichloride, palladium-bis-(benzonitrile) dichloride, palladium acetylacetonate and tetrakis-(triphenylphosphine)-palladium, and copper compounds, such as copper iodide, copper bromide, copper acetate and copper acetylacetonate.

Preferred phase transfer catalysts are quaternary ammonium and phosphonium salts, such as tetrabutylammonium chloride, bisulfate, hydroxide, bromide or iodide, benzyltriethylammonium chloride, cetyltrimethylammonium chloride or benzyltriphenylphosphonium chloride, or crown ethers, such as 12-crown-4, 15-crown-5 and 18-crown-6.

Starting materials are usually reacted with one another in stoichiometric amounts but, in order to increase the yield, it may be advantageous to use one of the starting materials in an excess of from 0.1 to 10, in particular from 0.2 to 1.5, mol equivalents. The catalysts are preferably used in from 0.01 to 0.2 molar amounts.

The reaction mixtures are worked up in a conventional manner, for example by adding water, separating the phases and purifying the crude products by column chromatography.

Process B

The compounds of the formula I are also obtained, for example, by converting a dibromoethane of the general formula IV in a conventional manner in an inert organic solvent in the presence of a base.

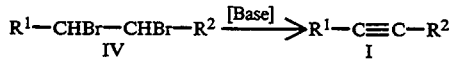

$$R^1-CHBr-CHBr-R^2 \xrightarrow{[Base]} R^1-C{\equiv}C-R^2$$
$$\text{IV} \qquad\qquad\qquad\qquad \text{I}$$

The reaction is carried out in general at from −20° to 110° C., preferably from 0° to 90° C.

Examples of suitable solvents are those stated above for process A. The following are particularly suitable: methanol, ethanol, propanol, 2-propanol and mixtures of these with water.

Suitable bases in this process are those mentioned above.

In view of the intended use of the compounds IA in insecticides and acaricides, suitable substituents are the following radicals:

$R^1$ is a five-membered heteroaromatic structure which contains from one to three nitrogen atoms and/or an oxygen or sulfur atom as hetero atoms, such as 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl or 1,3,4-triazol-2-yl, in particular 2-thienyl, 3-thienyl or 2-thiazolyl, which may carry from one to three of the following radicals:

nitro;

halogen, such as fluorine, chlorine, bromine or iodine, in particular fluorine;

$C_1$-$C_4$-alkyl, such as methyl, ethyl, propyl, 1-methylethyl, butyl, 1-methylpropyl, 2-methylpropyl or 1,1-dimethylethyl, in particular methyl, ethyl or 1-methylethyl;

$C_1$-$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, in particular trichloromethyl or trifluoromethyl;

$C_1$-$C_4$-alkoxy, such as methoxy, ethoxy, propoxy, 1-methylethoxy, butoxy, 1-methylpropoxy, 2-methylpropoxy or 1,1-dimethylethoxy, in particular methoxy, ethoxy or 1-methylethoxy;

$C_1$-$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, in particular trifluoromethoxy or pentafluoroethoxy;

$C_1$-$C_4$-alkylthio, such as methylthio, ethylthio, propylthio, 1-methylethylthio, butylthio, 1-methylpropylthio, 2-methylpropylthio or 1,1-dimethylethylthio, preferably methylthio;

$C_1$-$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio;

$C_3$-$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 2-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, preferably 2-propenyl, 2-butenyl, 2-methyl-2-propenyl, 2-pentenyl, 2-methyl-2-butenyl, 3-methyl-2-butenyl or 1,2-dimethyl-2-propenyl, in particular 2-propenyl, 2-butenyl or 3-methyl-2-butenyl;

or $C_3$–$C_8$-cycloalkyl, such as cyclopropyl, cyclobutyl, cyclopentyl, cyclohexyl, cycloheptyl, cyclooctyl, preferably cyclopropyl, cyclopentyl or cyclohexyl, in particular cyclopropyl, and $R^2$ is a mononuclear to trinuclear aromatic ring system, such as phenyl, 1-naphthyl or 2-naphthyl, which may carry from one to five halogen atoms, such as fluorine, chlorine, bromine or iodine, in particular fluorine or chlorine, and/or from one to three of the following groups: nitro, cyano, $C_1$–$C_4$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably $C_1$–$C_4$-alkyl, such as methyl, ethyl, propyl, 1-methylethyl, butyl, 1-methylpropyl, 2-methylpropyl or 1,1-dimethylethyl, in particular methyl or ethyl;

$C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, preferably trifluoromethyl;

$C_1$–$C_4$-alkoxy, such as methoxy, ethoxy, propoxy, 1-methylethoxy, butoxy, 1-methylpropoxy, 2-methylpropoxy or 1,1-dimethylethoxy, preferably methoxy or ethoxy, in particular methoxy;

$C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy;

$C_1$–$C_4$-alkylthio, such as methylthio, ethylthio, propylthio, 1-methylethylthio, butylthio, 1-methylpropylthio, 2-methylpropylthio or 1,1-dimethylethylthio, preferably methylthio;

$C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio;

$C_1$–$C_4$-alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl, in particular methoxycarbonyl or ethoxycarbonyl;

$C_3$–$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, preferably 2-propenyl, 2-butenyl or 2,3-dimethyl-2-butenyl; or phenyl or phenoxy, where the last-mentioned aromatic groups in turn may carry from one to five halogen atoms, such as fluorine, chlorine, bromine or iodine, preferably fluorine or chlorine, and/or from one to three of the following groups:

$C_1$–$C_4$-alkyl, such as methyl, ethyl, propyl, 1-methylethyl, butyl, 1-methylpropyl, 2-methylpropyl or 1,1-dimethylethyl, preferably methyl or ethyl;

$C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, preferably trifluoromethyl;

$C_1$–$C_4$-alkoxy, such as methoxy, ethoxy, propoxy, 1-methylethoxy, butoxy, 1-methylpropoxy, 2-methylpropoxy or 1,1-dimethylethoxy, preferably methoxy or ethoxy;

$C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy;

$C_1$–$C_4$-alkylthio, such as methylthio, ethylthio, propylthio, 1-methylethylthio, butylthio, 1-methylpropylthio, 2-methylpropylthio or 1,1-dimethylethylthio, preferably methylthio;

or $C_1$–$C_4$-haloalkylthio, in particular $C_1$- or $C_2$-haloalkylthio, such as chloromethylthio, dichloromethylthio, trichloromethylthio, fluoromethylthio, difluoromethylthio, fluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, preferably 2,2,2-trichloroethylthio.

Examples of particularly preferred acetylene derivatives of the general formula IA are shown in the table below.

TABLE $R^1-C\equiv C-R^2$  IA

| $R^1$ | $R^2$ |
|---|---|
| 2-Thienyl | Phenyl |
| 5-F-2-thienyl | Phenyl |
| 4-F-2-thienyl | Phenyl |
| 3-F-2-thienyl | Phenyl |
| 3,4-F$_2$-2-thienyl | Phenyl |
| 3-Thienyl | Phenyl |
| 4-Cl-2-thienyl | Phenyl |
| 5-Cl-2-thienyl | Phenyl |
| 3-Cl-2-thienyl | Phenyl |
| 3,4-Cl$_2$-2-thienyl | Phenyl |
| 5-Cl-3-thienyl | Phenyl |
| 4-Cl-3-thienyl | Phenyl |
| 5-Br-3-thienyl | Phenyl |
| 4-Br-2-thienyl | Phenyl |
| 5-CH$_3$-2-thienyl | Phenyl |
| 4-CH$_3$-2-thienyl | Phenyl |
| 3-CH$_3$-2-thienyl | Phenyl |
| 5-CH$_2$CH$_3$-2-thienyl | Phenyl |
| 3,5-(CH$_3$)$_2$-2-thienyl | Phenyl |
| 5-CH(CH$_3$)$_2$-2-thienyl | Phenyl |
| 4-CH(CH$_3$)$_2$-2-thienyl | Phenyl |
| 5-C(CH$_3$)$_3$-2-thienyl | Phenyl |
| 4-C(CH$_3$)$_3$-2-thienyl | Phenyl |
| 5-CH$_2$CH=CH$_2$-2-thienyl | Phenyl |
| 4-CH$_2$CH=CH$_2$-2-thienyl | Phenyl |
| 5-CH$_2$CH=C(CH$_3$)$_2$-2-thienyl | Phenyl |
| 5-CF$_3$-2-thienyl | Phenyl |
| 4-CF$_3$-2-thienyl | Phenyl |
| 3-CF$_3$-2-thienyl | Phenyl |
| 2-Thienyl | 4-F-phenyl |
| 2-Thienyl | 3-F-phenyl |
| 2-Thienyl | 3,4-F$_2$-phenyl |
| 2-Thienyl | 4-Cl-phenyl |
| 2-Thienyl | 3-Cl-phenyl |
| 2-Thienyl | 2-Cl-phenyl |
| 2-Thienyl | 3,4-Cl$_2$-phenyl |
| 2-Thienyl | 2,4-Cl$_2$-phenyl |
| 3-Thienyl | 4-Cl-phenyl |
| 2-Thienyl | 4-Br-phenyl |
| 3-Thienyl | 4-Br-phenyl |
| 2-Thienyl | 4-CH$_3$-phenyl |
| 2-Thienyl | 3-CH$_3$-phenyl |
| 2-Thienyl | 2-CH$_3$-phenyl |
| 2-Thienyl | 2,4-(CH$_3$)$_2$-phenyl |
| 3-Thienyl | 2,4-(CH$_3$)$_2$-phenyl |
| 5-Br-2-thienyl | 4-CH$_3$-phenyl |
| 4-Cl-2-Thienyl | 4-CH$_3$-phenyl |
| 2-Thienyl | 3,4-(CH$_3$)$_2$-phenyl |
| 2-Thienyl | 2,4,6-(CH$_3$)$_3$-phenyl |
| 2-Thienyl | 4-CH$_2$CH$_3$-phenyl |
| 2-Thienyl | 4-CH(CH$_3$)$_2$-phenyl |
| 2-Thienyl | 4-(CH$_2$)$_3$CH$_3$-phenyl |
| 2-Thienyl | 4-C(CH$_3$)$_3$-phenyl |
| 3-Thienyl | 4-CH$_2$CH(CH$_3$)$_2$-phenyl |
| 2-Thienyl | 3,5-(CH$_3$)$_2$-phenyl |
| 2-Thienyl | 4-(CH$_2$)$_4$CH$_3$-phenyl |
| 2-Thienyl | 4-CH$_2$C(CH$_3$)$_3$-phenyl |
| 2-Thienyl | 4-(CH$_2$)$_5$CH$_3$-phenyl |
| 2-Thienyl | 4-cyc-C$_3$H$_5$-phenyl |
| 2-Thienyl | 4-cyc-C$_5$H$_9$-phenyl |
| 2-Thienyl | 4-cyc-C$_6$H$_{11}$-phenyl |
| 3-Thienyl | 4-cyc-C$_6$H$_{11}$-phenyl |
| 2-Thienyl | 4-CH$_2$CH=CH$_2$-phenyl |
| 2-Thienyl | 4-CH$_2$CH=CHCH$_3$-phenyl |
| 2-Thienyl | 4-CH$_2$CH=C(CH$_3$)$_2$-phenyl |
| 2-Thienyl | 4-OCH$_3$-phenyl |
| 2-Thienyl | 3-OCH$_3$-phenyl |
| 2-Thienyl | 2-OCH$_3$-phenyl |
| 3-Thienyl | 4-OCH$_3$-phenyl |
| 2-Thienyl | 3,4-(OCH$_3$)$_2$-phenyl |
| 2-Thienyl | 2,4-(OCH$_3$)$_2$-phenyl |
| 2-Thienyl | 4-OCH$_2$CH$_3$-phenyl |
| 2-Thienyl | 4-O(CH$_2$)$_2$CH$_3$-phenyl |
| 3-Thienyl | 4-O(CH$_2$)$_3$CH$_3$-phenyl |
| 2-Thienyl | 4-C$_6$H$_5$-phenyl |
| 3-Thienyl | 4-C$_6$H$_5$-phenyl |
| 2-Thienyl | 3-C$_6$H$_5$-phenyl |
| 3-Thienyl | 3-OC$_6$H$_5$-phenyl |
| 2-Thienyl | 4-CF$_3$-phenyl |
| 3-Thienyl | 4-CF$_3$-phenyl |
| 3-Thienyl | 3-CF$_3$-phenyl |
| 2-Thienyl | 2-CF$_3$-phenyl |
| 2-Thienyl | 4-C$_6$H$_5$-phenyl |
| 3-Thienyl | 4-C$_6$H$_5$-phenyl |
| 2-Thienyl | 3-C$_6$H$_5$-phenyl |
| 3-Thienyl | 3-C$_6$H$_5$-phenyl |
| 2-Thienyl | 4-CN-phenyl |
| 2-Thienyl | 3-CN-phenyl |
| 2-Thienyl | 4-NO$_2$-phenyl |
| 2-Thienyl | 3-NO$_2$-phenyl |
| 2-Thiazolyl | Phenyl |
| 2-Thiazolyl | 4-Cl-phenyl |
| 2-Thiazolyl | 4-CH$_3$-phenyl |
| 2-Thiazolyl | 4-C(CH$_3$)$_3$-phenyl |
| 2-Thiazolyl | 4-OCH$_3$-phenyl |
| 2-Thiazolyl | 4-C$_6$H$_5$-phenyl |
| 2-Thiazolyl | 4-OC$_6$H$_5$-phenyl |
| 2-Thiazolyl | 4-F-phenyl |

The compounds of the formula IA are suitable for effectively controlling pests from the class consisting of the insects, arachnids and nematodes. They can be used as pesticides in crop protection, in the hygiene and veterinary sectors and for the protection of stored materials.

The insect pests include, from the order of the butterflies (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Hellothis virescens, Hellothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panoli flamea, Pectinophora gossypiella, Peridroma saucia, Phalera bucephala, Phthorimaea operculella, phyllocnistis citrella, Pieris brassicae, Plathypena scarbra, Plutella xylostella, pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;* from the order of the beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blas-*

*tophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia Japonica, Sitona lineatus* and *Sitophilus granaria;* from the order of the Diptera, for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilla cuprina, Lucilla sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa;* from the order of the Thysanoptera, for example *Franklinleila fusca, Franklinleila occidentalis, Franklinleila tritici, Scirtothrips citri, Thrips oryzae, Thrips palmi* and *Thrips tabaci;* from the order of the Hymenoptera, for example *Athalia rosae, Atta cephalotes, Atta sexdens, Atta texana, Hoplocampa minuta, Hoplocampa testudinea, Monomorium pharaonis, Solenopsis geminata* and *Solenopsis invicta;* from the order of the Heteroptera, for example Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis and *Thyanta perditor;* from the order of the Homoptera, for example *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mall, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii;* from the order of the Isoptera, for example *Calotermes flavicollis, Leucotermes flavipes, Reticulitermes lucifugus* and *Termes natalensis;* from the order of the Orthoptera, for example *Acheta domestica, Blatta orientalis, Blattella germanica, Forficula auricularia, Gryllotalpa gryllotalpa, Locusta migratoria, Melanoplus birittatus, Melanoplus femurrubrum, Melanoplus mexicanus, Melanoplus sanguinipes, Melanoplus spretus, Nomadacris septemfasciata, Priplaneta americana, Schistocerca americana, Schistocerca peregrina, Stauronotus maroccanus* and *Tachycines asynamorus;* from the class of the Arachnoidea, for example Acarina, such as *Amblyomma americanum, Amglyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobins megnini, Paratetranychus pilosus, Permanyssus gallinae, Phyllocaptrata oleivora, Polyphagotarsonemus latus, Psoroptes ovis, Rhipicephalus appendiculatus, Rhipicephalus evertsi, Saccoptes scabiei, Tetranychus cinnabarinus, Tetranychus kanzawai, Tetranychus pacificus, Tetranychus telarius* and *Tetranychus urticae.*

The active ingredients can be used as such, in the form of formulations or in the application forms prepared therefrom, for example in the form of directly sprayable solutions, powders, suspensions or dispersions, emulsions, oil dispersions, pastes, dusting agents, broadcasting agents or granules, by spraying, atomizing, dusting, broadcasting or pouring. The application forms depend entirely on the intended uses; they should in any case ensure very fine distribution of the novel active ingredients.

For the preparation of directly sprayable solutions, emulsions, pastes or oil dispersions, mineral oil fractions having a medium to high boiling point, such as kerosene or diesel oil, and coal tar oils and oils of vegetable and animal origin, aliphatic, cyclic and aromatic hydrocarbons, e.g. benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene, isophorone, strongly polar solvents, e.g. dimethylformamide, dimethyl sulfoxide, N-methylpyrrolidone or water, are suitable.

Aqueous application forms can be prepared from emulsion concentrates, pastes or wettable powders (spray powders, oil dispersions) by adding water. For the preparation of emulsions, pastes or oil dispersions, the substances as such or in solution in an oil or solvent can be homogenized in water by means of wetting agents, adhesives, dispersants or emulsifiers. However, it is also possible to prepare concentrates which consist of active substance, wetting agents, adhesives, dispersants or emulsifiers and possibly solvents or oil and which are suitable for dilution with water.

Suitable surfactants are alkali metal, alkaline earth metal and ammonium salts of ligninsulfonic acid, naphthalenesulfonic acid, phenolsulfonic acid, dibutylnaphthalenesulfonic acid, alkylarylsulfonates, alkylsulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of naphthalenesulfonic acid with phenol and formaldehyde, polyoxyethylene octylphenol ethers, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol ester, ligninsulfite waste liquors and methylcellulose.

Powders, broadcasting agents or dusting agents can be prepared by mixing or milling the active substances together with solid carriers.

The formulations contain in general from 0.01 to 95, preferably from 0.1 to 90, % by weight of the active ingredient. The active ingredients are used in a purity of from 90 to 100%, preferably from 95 to 100% (according to the NMR spectrum).

Examples of formulations are:

I. 5 parts by weight of compound No. 1.001 are thoroughly mixed with 95 parts by weight of finely divided kaolin. A dusting agent which contains 5% by weight of the active ingredient is obtained in this manner.

II. 30 parts by weight of compound No. 1.003 are thoroughly mixed with a mixture of 92 parts by weight of silica gel powder and 8 parts by weight of liquid paraffin, which was sprayed onto the surface of this silica gel. A formulation of the active ingredient having good adhesion and containing 23% by weight of active ingredient is obtained in this manner.

III. 10 parts by weight of compound No. 1.003 are dissolved in a mixture which consists of 90 parts by weight of xylene, 6 parts by weight of the adduct of from 8 to 10 moles of ethylene oxide with 1 mole of oleic acid N-monoethanolamide, 2 parts by weight of the calcium salt of dodecylbenzenesulfonic acid and 2 parts by weight of the adduct of 40 moles of ethylene oxide with 1 mole of castor oil (active ingredient content 9% by weight).

IV. 20 parts by weight of compound No. 1.003 are dissolved in a mixture which consists of 60 parts by weight of cyclohexanone, 30 parts by weight of isobutanol, 5 parts by weight of the adduct of 7 moles of ethylene oxide with 1 mole of isooctyl phenol and 5 parts by weight of the adduct of 40 moles of ethylene oxide with 1 mole of castor oil (active ingredient content 16% by weight).

V. 80 parts by weight of compound No. 1.001 are thoroughly mixed with 3 parts by weight of the sodium salt of diisobutylnaphthalene-α-sulfonic acid, 10 parts by weight of the sodium salt of a ligninsulfonic acid obtained from a sulfite waste liquor and 7 parts by weight of silica gel powder, and the mixture is milled in a hammer mill (active ingredient content 80% by weight).

VI. 90 parts by weight of compound No. 1.003 are mixed with 10 parts by weight of N-methyl-α-pyrrolidone, and a solution which is suitable for use in the form of very small drops is obtained (active ingredient content 90% by weight).

VII. 20 parts by weight of compound No. 1.001 are dissolved in a mixture which consists of 40 parts by weight of cyclohexanone, 30 parts by weight of isobutanol, 20 parts by weight of the adduct of 7 moles of ethylene oxide with 1 mole of isooctyl phenol and 10 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

VIII. 20 parts by weight of active ingredient No. 1.001 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

Granules, for example coated, impregnated and homogeneous granules, can be prepared by binding the active ingredients to solid carriers. Examples of solid carriers are mineral earths, such as silica gel, silicas, silicates, talc, kaolin, attaclay, limestone, lime, chalk, bole, loess, clay, dolomite, kieselguhr, calcium sulfate, magnesium sulfate, magnesium oxide, milled plastics, fertilizers, e.g. ammonium sulfate, ammonium phosphate, ammmonium nitrate and ureas, and vegetable products, such as cereal meal, ground bark, woodmeal and nutshell meal, cellulose powder and other solid carriers.

The active ingredient concentrations in the ready-to-use formulations can be varied within wide ranges.

In general, they are from 0.0001 to 10%, preferably from 0.01 to 1%.

The active ingredients can also be successfully used by the ultralow volume method (ULV), and it is possible to apply formulations containing more than 95% by weight of active ingredient or even the active ingredient without additives.

The application rate of active ingredient under open air conditions is from 0.01 to 10, preferably from 0.05 to 5, kg/ha.

Oils of various types, herbicides, fungicides, other pesticides and bactericides may be added to the active ingredients, if necessary also directly before use (tank mix). These agents can be mixed with the novel agents in a weight ratio of from 1:10 to 10:1.

Examples of Syntheses

The method described in the Example of Synthesis below was used to obtain further compounds IA, with appropriate modification of the starting compounds. The compounds thus obtained are shown in the table below, together with physical data.

EXAMPLE 1

1-(2-Thienyl)-2-phenylacetylene 1 g (0.00142 mol) of bis-(triphenylphosphine)palladium chloride, 5 g (0.0262 mol) of copper iodide and 8.5 g (0.0324 mol) of triphenylphosphine were added in succesion to a solution of 163 g (1 mol) of 2-bromothiophene and 127.5 g (1.25 mol) of phenylacetylene in 850 ml of triethylamine at 25° C. Stirring was carried out for twelve hours under a nitrogen atmosphere at 80° C., after which the mixture was filtered and the filtrate was evaporated down under reduced pressure. 600 ml of methylene chloride were added to the residue and the solution was washed with three times 200 ml of water, dried over $Na_2SO_4$ and evaporated down under reduced pressure, after which 200 ml of n-pentane were added. The crystals thus obtained were filtered off under suction and dried. 106 g (57.6% of theory) of 1-(2-thienyl)-2-phenylacetylene were obtained as pale yellow crystals of melting point 49°–59° C. (Active Ingredient Example 1.001).

TABLE 1

| No. | $R^1$—C≡C—$R^2$ IA $R^1$ | $R^2$ | mp. [°C.] |
|---|---|---|---|
| 1.001 | 2-Thienyl | Phenyl | 49–59 |
| 1.002 | 3-Thienyl | Phenyl | 47–49 |
| 1.003 | 3-Cl-2-thienyl | Phenyl | 21–24 |
| 1.004 | 2-Thiazolyl | Phenyl | 44–45 |

Use Examples

The insecticidal action of the compounds of the general formula IA were demonstrated by the following experiments:

The active ingredients were prepared a) as a 0.1% strength solution in acetone or b) as a 10% strength emulsion in a mixture of 70% by weight of cyclohexanol, 20% by weight of Nekanil ® LN (Lutensol ® AP6, wetting agent having an emulsifying and dispersing action and based on ethoxylated alkylphenols) and 10% by weight of Emulphor ® EL (Emulan ® EL, emulsifier based on ethoxylated fatty alcohols)

and were diluted to the desired concentration with acetone in the case of a) or with water in the case of b).

After the end of the experiments, the lowest concentration, in each case, at which the compounds still showed an 80–100% inhibition or kill rate (activity threshold or minimum concentration (mg)) in comparison with untreated control experiments was determined.

A. *Hellothis virescens*, ovolarvicidal action

Pieces of bush bean leaves are first wet with the aqueous active ingredient formulation and then infested with about 15 Heliothis eggs in a Petri dish (the eggs should be no older than 24 hours).

After 4 days, the hatching and kill rate of young caterpillars are evaluated.

In this test, compounds 1.001 and 1.003 had activity thresholds of 1,000 and 400 ppm, respectively.

B. *Prodenia litura*, breeding experiment

Five caterpillars in development stage L3 (10–12 mm) which had suffered no detectable damage in the contact experiment are placed on standard nutrient medium wet with the active ingredient.

Observation continues until hatching of the butterflies in a control experiment without active ingredient.

In this test, compounds 1.001 and 1.003 had activity thresholds of 1.0 and 0.04 ppm, respectively.

We claim:

1. An acetylene derivative of the formula I $$R^1-C\equiv C-R^2 \quad \text{I}$$

where $R^1$ is 2-thienyl, 3-thienyl or 2-thiazolyl which may carry from one to three of the following radicals: nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_6$-alkenyl or $C_3$–$C_8$-cycloalkyl, $R^2$ is a mononuclear to trinuclear aromatic ring system which may carry from one to five halogen atoms or from one to three of the following groups: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkoxycarbonyl, $C_1$–$C_4$-alkenyl, phenyl or phenoxy, where the last-mentioned aromatic groups may in turn carry from one to five halogen atoms or from one to three of the following groups: $C_1$–$C_4$ alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio, and $R^1$ is not 2-thienyl when $R^2$ is phenyl or 4-methylphenyl, $R^1$ is not 2-thienyl when $R^2$ is thienyl substituted by $C_1$–$C_4$-alkoxy carbonyl, and $R^1$ is not 2-thiazolyl when $R^2$ is phenyl.

2. An insecticide or acaricide containing an effective amount of an acetylene derivative of the formula I as claimed in claim 1 and inert additives.

* * * * *